United States Patent [19]

Sharp et al.

[11] 3,976,786

[45] Aug. 24, 1976

[54] METHOD OF PREVENTING COCCIDIOSIS WITH 3,5-DINITROANILINE DERIVATIVES AND VETERINARY COMPOSITIONS CONTAINING SUCH DERIVATIVES

[75] Inventors: Brian William Sharp, Hornchurch; Dennis Warburton, Brentwood; Raymond Barry Williams, Upminster; Kenneth Robert Harry Wooldridge, Brentwood, all of England

[73] Assignee: May & Baker Limited, England

[22] Filed: July 23, 1975

[21] Appl. No.: 598,534

Related U.S. Application Data

[62] Division of Ser. No. 453,643, March 21, 1974, Pat. No. 3,911,011.

[30] Foreign Application Priority Data

Mar. 23, 1973 United Kingdom............... 14191/73

[52] U.S. Cl. .............................................. 424/324
[51] Int. Cl.² ....................................... A61K 31/165
[58] Field of Search ..................................... 424/324

[56] References Cited
UNITED STATES PATENTS 3,008,873  11/1961  Rogers et al. ...................... 424/322

Primary Examiner—Sam Rosen
Attorney, Agent, or Firm—Stevens, Davis, Miller & Mosher

[57] ABSTRACT

Compounds of the formula:

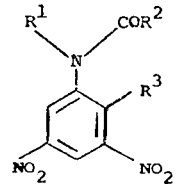

wherein $R^1$ represents hydrogen, methyl, ethyl, n-propyl, iso-propyl, n-butyl, iso-butyl or sec-butyl, $R^2$ represents hydrogen or alkyl of 1 through 4 carbon atoms or cycloalkyl of 3 or 4 carbon atoms, and $R^3$ represents hydrogen, methyl or ethyl, all of which are novel except for three compounds, have been found to be of use in the prevention of coccidiosis in chickens.

15 Claims, No Drawings

METHOD OF PREVENTING COCCIDIOSIS WITH 3,5-DINITROANILINE DERIVATIVES AND VETERINARY COMPOSITIONS CONTAINING SUCH DERIVATIVES

This is a division of application Ser. No. 453,643, filed Mar. 21, 1974, now U.S. Pat. No. 3,911,011.

This invention relates to dinitroaniline derivatives which are of use in the prevention of coccidiosis in chickens.

Coccidiosis, a disease caused by infections by protozoan parasites of the genus Eimeria, is one of the most important potential causes of economic loss in chicken flocks, particularly those raised under intensive conditions. The disease has a world-wide incidence and may occur wherever poultry are reared, and, if left untreated, often causes extensive loss of fowl. Economic loss results not only from mortality of the infected birds but also morbidity which may manifest itself in depression of body growth rate, reduction of food conversion efficiency and a general deterioration which is found in the carcass at slaughter. The elimination or control of coccidiosis is, therefore, of the utmost importance in successful chicken raising. Although other species occur in the chicken, the following five species of Eimeria, namely *E. tenella, E. acervulina, E. necatrix, E. burnetti* and *E. maxima*, are generally regarded as being responsible for the economic losses due to cocciodiosis in the rearing of chickens.

Infections with *E. tenella*, which is responsible for a severe infection of the caecum of chickens, and *E. necatrix* frequently result in mortality while infections due to the other three species are less frequently the cause of mortality but nevertheless result in economic loss due to depression of growth rate, feed-conversion efficiency and carcass deterioration. *E. tenella* and *E. necatrix* have generally been regarded in the past as being the most important species and efforts in the selection of anti-coccidial agents have been directed primarily towards the control of these species. In recent years it has been found, however, that while the control of *E. tenella* and *E. necatrix* remains an important problem, the incidence of disease caused by *E. acervulina, E. maxima* and *E. brunetti* has increased, thereby increasing the importance of their control.

An additional problem, which is encountered in the control of coccidiosis and is of increasing importance, is the emergence of strains of Eimeria which are resistant to anti-coccidial agents which normally control the species in question.

This problem of resistance has been found to a greater or lesser extent with all anti-coccidial agents which have been used commercially on a wide scale and may arise from severe infection challenges and the selection of inherently more resistant coccidia by the control of more susceptible organisms by the anti-coccidial agents.

In addition to controlling the disease, it is naturally important that an anti-coccidial agent should be well tolerated at dose levels which are used and should have no adverse effect upon the health of the birds to which it is administered. As a result of research and experimentation, it has been found that 3,5-dinitroaniline derivatives of the general formula:

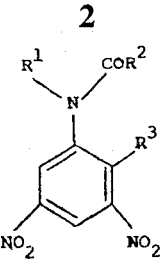

wherein $R^1$ represents a hydrogen atom or a methyl, ethyl, n-propyl, iso-propyl, n-butyl, iso-butyl or sec-butyl group, $R^2$ represents a hydrogen atom, a straight- or branched-chain alkyl group containing from 1 to 4 carbon atoms or a cycloalkyl group containing 3 or 4 carbon atoms, and $R^3$ represents a hydrogen atom or a methyl or ethyl group, possess useful activity against Eimeria, particularly *Eimeria tenella* and *Eimeria acervulina*, infections of chickens and are useful in the prevention of coccidiosis in chickens.

Compounds of special value in this respect are those compounds of formula I wherein $R^1$ and $R^3$ represent hydrogen atoms while $R^2$ represents a hydrogen atom or a methyl, ethyl or iso-propyl group and those compounds of formula I wherein $R^3$ represents a hydrogen atom and $R^2$ represents a methyl group while $R^1$ represents a methyl or ethyl group, that is to say individual compounds of particular importance are 3',5'-dinitroacetanilide, 3',5'-dinitro-N-ethylacetanilide, 3',5'-dinitroformanilide, 3',5'-dinitropropionanilide, 3',5'-dinitro-iso-butyranilide and, more especially, 3',5'-dinitro-N-methylacetanilide.

According to the present invention there is provided a method for the prevention of coccidiosis in chickens, more particularly coccidiosis caused by infections of *Eimeria tenella* and *Eimeria acervulina*, which comprises administering to the birds a prophylacetically-effective amount of one or more of the compounds of general formula I. According to a preferred embodiment, the compounds of general formula I are administered in the diet of chickens in an amount equal to between 0.0025 and 0.05%, preferably between 0.00625 and 0.025%, by weight of the food consumed.

According to a feature of the present invention there are provided veterinary compositions useful for the prevention of coccidiosis in chickens, comprising one or more of the componds of formula I, as active ingredient, in association with a physiologically innocuous carrier (i.e. a carrier which is not harmful to the chickens at the dosages used) which may be solid, semi-solid or a liquid. Such compositions are conveniently produced by intimately dispersing the active ingredient through the carrier, if necessary, where the carrier is a liquid in which the active ingredient is but sparingly soluble, e.g. water, using an emulsifying, dispersing, suspending or wetting agent.

Preferred compositions are solids or semi-solids in which the carrier is provided at least in part by a chicken feedstuff, i.e. an organic or mineral substance which is intended to be fed to the chicken; that is to say, the active ingredient may be incorporated in a solid or semi-solid feedstuff. Incorporation of the active ingredient in the feedstuff, which may be a commercial starter, grower, layer or breeder feed, may be effected by any conventional method such as stirring, tumbling or grinding. Compositions of varying concentrations can be prepared by altering the ratio of carrier to active ingredient. The active ingredient may also be incorporated in the feedstuff in the form of a powder concentrate containing active ingredient and a solid, physiologically innocuous carrier, e.g. wheat middlings, talc, kaolin or chalk or a diatomaceous earth, such as kieselguhr, or a mixture thereof, and such compositions are also included within the scope of this invention. These compositions may also contain agents to promote adhesion of the active ingredient to the carrier, for example soya oil. To the active ingredient or powders containing it, there may be added before admixture with the feedstuff, one or more physiologically innocuous wetting and/or dispersing agents, for example, the condensation product of $\beta$-naphthalenesulphonic acid and formaldehyde, sodium lauryl sulphate or polyoxyethylene(20)sorbitan monooleate. Alternatively, when a wetting, suspending, emulsifying or dispersing agent is added to the active ingredient or powder, the compositions so obtained may be mixed with water to provide stable dispersions suitable for addition to feedstuffs.

Compositions suitable for addition to feedstuffs which comprise the active ingredient in association with a wetting, suspending, dispersing or emulsifying agent, with or without a physiologically innocuous carrier, are also included within the scope of this invention.

Liquid compositions may be dispersions of the active ingredient in drinking water, and these compositions may be prepared from concentrates which may be added to water, or are self-emulsifying with water. Such concentrates comprise the active ingredient in association with one or more wetting, suspending, dispersing, emulsifying, thickening or gelling agents, with or without a physiologically innocuous carrier, or in association with a water-soluble physiologically innocuous carrier, and are included within the scope of this invention. Examples of these concentrates are:

1. Mixtures of the active ingredient with a wetting, dispersing, thickening or gelling agent or a combination of such agents with or without a water-soluble physiologically innocuous carrier, e.g. water;
2. Powders comprising the active ingredient, a physiologically innocuous carrier, and a wetting, suspending or dispersing agent;
3. Stable dispersions obtained by mixing concentrates of types (1) or (2) with water; and
4. Mixtures of the active ingredient with a water-soluble physiologically innocuous carrier, e.g. sucrose or glucose.

Suitable dispersing agents include ethylene oxide/glyceride oil condensates, ethylene oxide/fatty alkylamine condensates and polyoxyethylene(20)sorbitan monooleate. Suitable thickening agents include sodium carboxymethylcellulose and water-soluble gums, e.g. gum tragacanth. Finely divided attapulgite clays may be used as gelling agents.

It is also possible to administer the anti-coccidial agents of the present invention orally to chickens in the form of granules, pellets, suspensions, solutions and emulsions comprising the active ingredient in association with suitable physiologically innocuous carriers and adjuvants. Such administration is, however, generally less convenient and therefore such compositions are not preferred.

Concentrates for addition to chicken feed generally contain from about 1 to about 90% by weight of the active ingredient and preferably about 4–50% by weight absorbed on or mixed with a carrier. Feedstuffs generally contain between about 0.0025 and about 0.05%, more especially between about 0.00625 and about 0.025%, of active ingredient by weight of the food consumed. Such relatively small amounts may be conveniently incorporated in the normal ration prior to feeding the chickens.

The compositions of the invention may, with advantage, also contain one or more additional prophylactic or therapeutic agents, for example furazolidone or other anti-coccidial agents such as 1-(4-amino-2-propyl-5-pyrimidinylmethyl)-2-picolinium chloride hydrochloride (amprolium), 2-sulphanilamidoquinoxaline (sulphaquinoxaline), 5-nitro-2-furaldehyde semicarbazone (nitrofurazone), quinoline-3-carboxylate anticoccidial agents, e.g. ethyl 6,7-diisobutoxy-4-hydroxyquinoline-3-carboxylate (buquinolate), ethyl 6-n-decyloxy-7-ethoxy-4-hydroxyquinoline-3-carboxylate (decoquinate) and methyl 7-benzyloxy-6-n-butyl-4-hydroxyquinoline-3-carboxylate (methyl benzoquate), and 3,5-dichloro-2,6-dimethyl-4-pyridinol(clopidol), 2-methyl-3,5-dinitrobenzamide (zoalene), 1,3-bis(p-chlorobenzylidinamino)quanidine (robenidine), monensin and ethyl 2-{2,3-dimethyl-2-[4-(3-pyrrolidin-1'-ylpropyl)thiosemicarbazono]ethylidene} hydrazinecarbodithioate.

Also they may contain other substances known to be useful as antibacterial agents and in promoting the growth of poultry or their egg production such as, for example, 4-hydroxy-3-nitrophenylarsonic acid, 1,5-bis(5-nitro-2-furyl)1,4-pentadien-3-one amidinohydrazone hydrochloride (nitrovin), zinc bacitracin and virginiamycin.

The following Examples illustrate compositions according to the present invention:

EXAMPLE 1

3',5'-Dinitroacetanilide (5 parts by weight) was added to wheat flour (20 parts by weight). The mixture was ground and incorporated in a suitable feedstuff for chickens to give a final concentration of about 0.0125% w/w of 3',5'-dinitroacetanilide. The treated foodstuff was suitable for feeding to chickens to prevent coccidiosis.

Similar compositions may be prepared by replacing the 3',5'-dinitroacetanilide by 3',5'-dinitroformanilide or by 3',5'-dinitropropionanilide.

EXAMPLE 2

3',5'-Dinitro-N-methylacetanilide (5 parts by weight) was added to wheat flour (20 parts by weight). The mixture was ground and incorporated in a suitable feedstuff for chickens to give a final concentration of about 0.01% w/w of 3',5'-dinitro-N-methylacetanilide. The treated foodstuff was suitable for feeding to chickens to prevent coccidiosis.

Similar compositions may be prepared by replacing the 3',5'dinitro-N-methylacetanilide by any other of the compounds of formula I.

The compounds of general formula I wherein $R^1$, $R^2$ and $R^3$ are as hereinbefore defined, with the exception of 3',5'-dinitroformanilide, 3',5'-dinitroacetanilide and 3',5'-dinitropropionanilide, are novel compounds which have not hitherto been disclosed in the literature. The present invention accordingly provides, as a feature of it, new 3,5-dinitroaniline derivatives of the general formula:

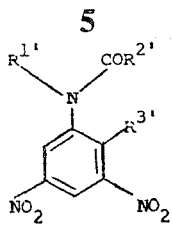

II wherein $R^{1'}$, $R^{2'}$ and $R^{3'}$ have the meanings hereinbefore specified in relation to symbols $R^1$, $R^2$ and $R^3$ respectively, $R^{3'}$ being a methyl or ethyl group when $R^{1'}$ is a hydrogen atom and $R^{2'}$ is a hydrogen atom or a methyl or ethyl group.

The disclosures in the literature of 3',5'-dinitroformanilide, 3',5'-dinitroacetanilide and 3',5'-dinitropropionanilide do not mention their useful activities against coccidia, but they do mention associations of these three compounds with water and with ethanol. Accordingly, veterinary compositions which are associations of either 3',5'-dinitroformanilide, 3',5'-dinitroacetanilide or 3',5'-dinitropropionanilide with either water or ethanol alone are outside the scope of the present invention.

The literature also discloses certain associations of 3',5'-dinitroformanilide, 3',5'-dinitroacetanilide and 3',5'-dinitropropionanilide with substances which are not normally suitable for use as carrier in a veterinary composition, i.e. acetic anhydride, acetic acid, diethyl ether, alkyl halides, ligroin, methanol, potassium hydroxide, sulphuric acid, nitric acid, and bromine.

As a further feature of the present invention, the novel compounds of general formula II are prepared by the acylation of compounds of the general formula:

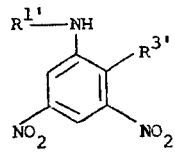

III wherein $R^{1'}$ and $R^{3'}$ are as hereinbefore defined. Generally the acylation is effected by the action of a compound of the general formula:

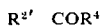    IV

[wherein $R^{2'}$ is as hereinbefore defined and $R^4$ represents a hydroxy group or, when $R^{2'}$ represents an alkyl or cycloalkyl group, $R^4$ preferably represents a halogen (e.g. chlorine or bromine) atom or a group —CCCR$^{2'}$, $R^{2'}$ being as hereinbefore defined in respect of general formula II] optionally in the presence of a solvent. When $R^{1'}$ and $R^{3'}$ in the starting materials of general formula III represent hydrogen atoms, it will be appreciated that $R^{2'}$ in general formula IV will be other than a hydrogen atom or a methyl or ethyl group as otherwise the 3,5-dinitroaniline products would not conform to general formula II.

When $R^4$ represents a hydroxy group or a group —OOCR$^{2'}$, the reaction is preferably carried out in the presence of a strong mineral acid, for example a catalytic quantity of concentrated sulphuric acid. When $R^4$ represents a halogen atom, the reaction is preferably carried out in the presence of a base, for example an aqueous alkali metal hydroxide (e.g. aqueous sodium hydroxide), or a tertiary amine (e.g. pyridine or triethylamine) which may also act as solvent medium.

As a further feature of the present invention, the novel compounds of general formula II wherein $R^1$ represents an alkyl group are prepared by N-alkylation of compounds of the general formula:

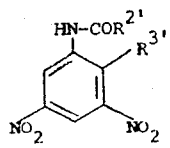

V wherein $R^{2'}$ and $R^{3'}$ are as hereinbefore defined. Generally the alkylation is effected by the action of a compound of the general formula:

    VI (wherein $R^{1'}$ represents a methyl, ethyl, n-propyl, iso-propyl, n-butyl, iso-butyl or sec-butyl group, and X represents the acid residue of a reactive ester, for example a halogen, e.g. iodine, bromine or chlorine, atom or a sulphuric or sulphonic acid residue) optionally in the presence of a solvent, for example dimethylformamide or an alkanol having at most 4 carbon atoms, e.g. methanol, or in the presence of a base and a solvent, for example in the presence of sodium in liquid ammonia or of an alkali metal carbonate in dimethyl sulphoxide. The reaction is generally carried out at a temperature between −80°C. and +100°C. preferably between −40°C. and +30°C.

As a still further feature of the present invention, the novel compounds of general formula II, wherein $R^{1'}$ represents a hydrogen atom, $R^{2'}$ represents an alkyl group containing from 1 to 4 carbon atoms or a cycloalkyl group containing 3 or 4 carbon atoms, and $R^{3'}$ represents a hydrogen atom or a methyl or ethyl group, $R^{3'}$ being a methyl or ethyl group when $R^{2'}$ is a methyl or ethyl group, are prepared by effecting the Beckmann rearrangement of compounds of the general formula:

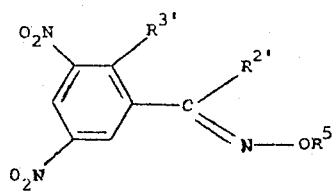

VII (wherein $R^{2'}$ and $R^{3'}$ are as immediately hereinbefore defined in respect of general formula II, and $R^5$ represents a hydrogen atom, a straight- or branched-chain alkyl or alkanoyl group containing up to 6 carbon atoms, or an arylsulphonyl group, e.g. a benzenesulphonyl or p-toluenesulphonyl group). When $R^{2'}$ in the starting materials of general formula VII represents a methyl or ethyl group, $R^{3'}$ must be a methyl or ethyl group in order to obtain a new 3,5-dinitroaniline product conforming to general formula II. Conditions suitable for effecting the Beckmann rearrangement of ketoximes to amides in general are well known in the art and are described, for example, in the review by Donaruma, Organic Reactions, 11, 1–156. Compounds of formula II are generally prepared from compounds of formula VII by the action of an acid, e.g. phosphorus pentachloride or concentrated sulphuric acid, usually in the presence of an organic solvent such as diethyl ether at a temperature between 0°C. and 150°C.

Compounds of general formulae III, IV, V, VI and VII may be prepared by the application or adaptation of well-known methods, that is to say methods hitherto used or described in the literature.

The following Examples illustrate the preparation of novel compounds of the present invention.

EXAMPLE 3 iso-Butyryl chloride (6.3 ml.) was added dropwise during 15 minutes to a stirred solution of 3,5-dinitroaniline (5.5 g.) in a mixture of dimethylformamide (18 ml.) and dry pyridine (18 ml.) maintained at a temperature of 0°–5°C. The reaction mixture was allowed to warm to room temperature during 30 minutes and then added to a mixture of ice and water (200 ml.). The precipitate was filtered off, dissolved in dimethylformamide (50 ml.) and added to a mixture of ice and water (300 ml.) containing concentrated hydrochloric acid (10 ml.). The precipitate was filtered off, washed with saturated aqueous sodium bicarbonate solution and then with water and dried. Crystallisation from aqueous ethanol gave 3',5'-dinitro-iso-butyranilide (5.6 g.), m.p. 165°–168°C.

By proceeding in a similar manner, but substituting n-butyryl chloride for the iso-butyryl chloride used as starting material, there was prepared 3',5'-dinitro-n-butyrylanilide, m.p. 97°–98°C. By again proceeding in a similar manner, but using 3,5-dinitro-2-methylaniline in dry tetrahydrofuran in place of the 3,5-dinitroaniline in dimethylformamide and acetyl chloride in place of the butyryl chloride, there was prepared 3',5'-dinitro-2'-methylacetanilide, m.p. 157°–159°C.

The 3,5-dinitro-2-methylaniline used as a starting material was prepared as follows:

Chloroform (38 ml.) was added carefully to a stirred mixture of oleum (16.9 ml.: 20% free sulphur trioxide) and concentrated sulphuric acid (3.8 ml.) followed by 3,5-dinitro-2-methylbenzoic acid (10.0 g.). The mixture was warmed to 45°C. and sodium azide (3.28 g.) was added in small portions over 20 minutes, the temperature of the reaction mixture being kept between 45° and 50°C. by means of intermittent cooling. After the addition was complete, the mixture was stirred and heated under reflux for 1 hour on the steam bath and then the chloroform was removed by decantation and the residue was poured into ice-water (300 ml.). The yellow precipitate was filtered off, washed with water and dried, to give crude 3,5-dinitro-2-methylaniline (8.8 g.), m.p. 169°–171°C. The crude product was dissolved in ethyl acetate, washed with saturated aqueous sodium bicarbonate solution and then with water and the solvent was removed in vacuo. Trituration with petroleum ether (b.p. 40°–60°C.) gave 3,5-dinitro-2-methylaniline (7.5 g.), m.p. 172.5°–174.5°C.

EXAMPLE 4

A mixture of 3,5-dinitroacetanilide (6.76 g.), anhydrous potassium carbonate (6.22 g.), methyl iodide (2.82 ml.) and dry dimethylsulphoxide (27 ml.) was stirred for 18 hours at room temperature in a stoppered flask. The reaction mixture was then diluted with water (150 ml.) and allowed to stand for a few minutes. The crystalline solid was filtered off and washed with water. The solid was recrystallised from a mixture of petroleum ether (b.p. 60°–80°C.) and benzene, and then from ethanol, to give 3',5'-dinitro-N-methylacetanilide (2.53 g.), m.p. 134.5°–136°C.

EXAMPLE 5

A stirred suspension of N-n-butyl-3,5-dinitroaniline (5.5 g.) in acetic anhydride (20 ml.) was treated with a few drops of concentrated sulphuric acid and then heated on the steam bath for 3 hours. The cooled reaction mixture was added to ice-water (400 ml.) and the product was extracted with ethyl acetate (3 × 100 ml.). The combined organic extract was washed with 2N aqueous sodium bicarbonate solution, dried with anhydrous magnesium sulphate, and the solvent removed in vacuo, to give 3',5'-dinitro-N-n-butylacetanilide (2.8 g.), in the form of an amber syrup, $\nu 1670$ cm$^{-1}$.

EXAMPLE 6

Sodium hydride (50% in mineral oil; 1.44 g.), followed by ethyl iodide (3.6 ml.), were added, in small portions during 2 minutes, to a warm stirred solution of 3',5'-dinitroacetanilide (6.75 g.) in dimethylformamide (20 ml.). The mixture was heated on the steam bath for 150 minutes, then cooled, poured into water (400 ml.) and extracted with ethyl acetate (3 × 100 ml.). The combined organic extracts were washed with water, dried over anhydrous magnesium sulphate and evaporated to dryness. The residue was purified by chromatography on alumina (150 g.) using benzene as the eluant. The fractions containing the required product were combined, evaporated to dryness and the residue crystallised from ethanol, to give 3',5'-dinitro-N-ethylacetanilide (4.2 g.), m.p. 126°–127°C.

By proceeding in a similar manner, but substituting n-propyl iodide for the ethyl iodide, there was prepared 3',5'-dinitro-N-n-propylacetanilide, m.p. 98°–100°C.

EXAMPLE 7

Methyl iodide (21.4 g.) was added to a mixture of 3,5-dinitroformanilide (19.0 g.) and anhydrous methanol (145 ml.), and the mixture was heated under reflux for 2 hours. The mixture was poured into ice-water and the deep orange precipitate was filtered off. Crystallisation from methanol gave 3,5-dinitro-N-methylaniline, m.p. 153°–154°C., as a by-product. The mother liquors from the crystallisation were evaporated to small bulk, glacial acetic acid (100 ml.) was added and the solution was poured into ice-water (200 ml.). The precipitate was filtered off and discarded. The filtrate was treated with anhydrous sodium carbonate. The pale yellow flocculent precipitate was filtered off and crystallised from methanol to give 3',5'-dinitro-N-methylformanilide (2 g.), m.p. 93°–94°C.

EXAMPLE 8

A mixture of 3,5-dinitroaniline (5.0 g.), cyclopropanecarboxylic anhydride (15 ml.) and two drops of concentrated sulphuric acid was warmed on the steam bath for 5 minutes and then allowed to stand for 2 hours at room temperature. The reaction mixture was diluted with diethyl ether (200 ml.), the colourless crystalline precipitate was filtered off, and crystallised from methanol containing a small amount of water, to give 3',5'-dinitrocyclopropanecarboxanilide (2.8 g.), m.p. 147°–149°C.

EXAMPLE 9

A mixture of formic acid (10 ml.) and acetic anhydride (5 ml.) was stirred at room temperature for 30 minutes. N-methyl-3,5-dinitroaniline (5.0 g.) was then added and the reaction mixture was heated on a steam bath for 10 minutes. The mixture was allowed to cool to room temperature during 40 minutes, then poured into ice-water and the precipitate was filtered off. Recrystallisation from methanol gave 3',5'-dinitro-N-methylformanilide (2.2 g.), m.p. 93°–94°C.

The following Procedures illustrate the preparation of compounds of general formula I which have been hitherto described in the literature.

PROCEDURE 1

A mixture of 3,5-dinitroaniline (12.8 g.) and acetic anhydride (64 ml.) was stirred during the dropwise addition of concentrated sulphuric acid (1.0 ml.). The temperature of the reaction mixture rose to about 45°C., and afer a few minutes colourless crystals were deposited. Afer 1 hour the reaction mixture was diluted with diethyl ether (200 ml.) and the crystalline solid was filtered off. Recrystallisation from a mixture of ethanol and water (2:1 by volume) gave 3',5'-dinitroacetanilide (11.5 g.) in the form of colourless plates, m.p. 191°–193°C.

By proceeding in a similar manner, but substituting n-propionic anhydride for the acetic anhydride used as a starting material, there was prepared 3',5'-dinitropropionanilide, m.p. 159°–160°C.

PROCEDURE 2

Acetic anhydride (6.0 ml.) was added to formic acid (98–100% w/v; 24.0 ml.) with swirling and cooling and the mixture was allowed to stand at room temperature for 30 minutes. 3,5-Dinitroaniline (6.0 g.) was then added. The reaction mixture was warmed for 5 minutes on the steam bath and allowed to stand for 40 minutes, allowing it to cool to room temperature. Water (100 ml.) was added, and the precipitate was filtered off and dried. Crystallisation from a mixture of petroleum ether (b.p. 60°–80°C.) and ethyl acetate (2:1 by volume) gave 3',5'-dinitroformanilide (4.1 g.), m.p. 121°–123°C.

PROCEDURE 3

Phosphorus pentachloride (1.0 g.) was added to a stirred solution of 3',5'-dinitroacetophenoxime (1.0 g.) in dry diethyl ether (20 ml.) at about 5°C. The temperature of the through an was allowed to rise to about 25°C. over 1 hour, and then dry acetonitrile (10 ml.) was added and the temperature of the mixture was raised to 35°C. for 15 minutes. The mixture, after cooling, was added to ice-water (50 ml.) and allowed to stand for a few minutes. The product was extracted with chloroform (3 × 50 ml.), and the combined organic extracts were dried over anhydrous magnesium sulphate and evaporated to dryness in vacuo. The residue was purified by passage throughan alumina column (20 g.) using ethyl acetate as eluant. The purified solution (300 ml.) was evaporated to dryness and the residue crystallised from ethanol, giving 3',5'-dinitroacetanilide (0.43 g.), m.p. 189°–191°C.

We claim:

1. A method of preventing coccidiosis in chickens which comprises administering orally to said chickens a prophylactically-effective amount of at least one 3,5-dinitroaniline derivative of the formula:

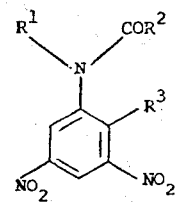

wherein $R^1$ is hydrogen, methyl, ethyl, n-propyl, iso-propyl, n-butyl, iso-butyl or sec-butyl, $R^2$ is hydrogen, alkyl of 1 through 4 carbon atoms or cycloalkyl of 3 or 4 carbon atoms, and $R^3$ is hydrogen, methyl or ethyl.

2. A method according to claim 1 in which the said 3,5-dinitroaniline derivative is administered in the diet of chickens in an amount equal to between 0.0025 and 0.05% by weight of the food consumed.

3. A method according to claim 1 in which the said 3,5-dinitroaniline derivative is 3',5'-dinitro-N-methylacetanilide.

4. A method according to claim 1 in which the said 3,5-dinitroaniline derivative administered to the chickens is selected from the class consisting of 3',5'-dinitroacetanilide, 3',5'-dinitro-N-ethylacetanilide, 3',5'-dinitroformanilide, 3',5'-dinitropropionanilide and 3',5'-dinitro-iso-butyranilide.

5. A method according to claim 1 in which the said 3,5-dinitroaniline derivative is administered to chickens to prevent coccidiosis caused by infections of *Eimeria tenella* or *Eimeria acervulina*.

6. A veterinary composition suitable for administration to chickens to prevent coccidiosis which comprises an effective amount of at least one 3,5-dinitroaniline derivative of the formula:

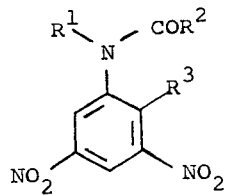

wherein $R^1$ is hydrogen, methyl, ethyl, n-propyl, iso-propyl, n-butyl, iso-butyl or sec-butyl, $R^2$ is hydrogen, alkyl of 1 through 4 carbon atoms or cycloalkyl of 3 or 4 carbon atoms, and $R^3$ is hydrogen, methyl or ethyl, in association with a physiologically innocuous carrier, the carrier being other than water or ethanol alone when the 3,5-dinitroaniline derivative is one wherein $R^1$ and $R^3$ are hydrogen atoms and $R^2$ is hydrogen, methyl or ethyl.

7. A veterinary composition according to claim 6 in which the carrier is a chicken feedstuff.

8. A chicken feedstuff according to claim 7 in which the concentration of the said 3,5-dinitroaniline derivative is from 0.0025 to 0.05% by weight of the feedstuff.

9. A veterinary composition according to claim 6 in which the said 3,5-dinitroaniline derivative is 3',5'-dinitro-N-methylacetanilide.

10. A veterinary composition according to claim 6 in which the said 3,5-dinitroaniline derivative is selected from the class consisting of 3',5'-dinitroacetanilide, 3',5'-dinitro-N-ethylacetanilide, 3',5'-dinitroformanilide, 3',5'-dinitropropionanilide and 3',5'-dinitro-isobutyranilide.

11. A concentrate for addition to chicken feedstuff or drinking water comprising 1 to 90% by weight of at least one 3,5-dinitroaniline derivative of the formula:

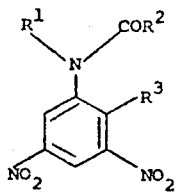

wherein $R^1$ is hydrogen, methyl, ethyl, n-propyl, isopropyl, n-butyl, iso-butyl or sec-butyl, $R^2$ is hydrogen, alkyl of 1 through 4 carbon atoms or cycloalkyl of 3 or 4 carbon atoms, and $R^3$ is hydrogen, methyl or ethyl, in association with a physiologically innocuous carrier, the carrier being other than water or ethanol alone when the 3,5-dinitroaniline derivative is one wherien $R^1$ and $R^3$ are hydrogen atoms and $R^2$ is hydrogen, methyl or ethyl.

12. A concentrate according to claim 11 containing from 4 to 50% by weight of 3,5-dinitroaniline derivative.

13. A concentrate according to claim 11 which also comprises an emulsifying, dispersing, suspending or wetting agent.

14. A concentrate according to claim 11 in which the included 3,5-dinitroaniline derivative is 3',5'-dinitro-N-methylacetanilide.

15. A concentrate according to claim 11 in which the included 3,5-dinitroaniline derivative is selected from the class consisting of 3',5'-dinitroacetanilide, 3',5'-dinitro-N-ethylacetanilide, 3',5'-dinitroformanilide, 3',5'-dinitro-propionanilide and 3',5'-dinitro-isobutyranilide.

* * * * *